United States Patent [19]

Cavalleri et al.

[11] 4,328,316
[45] May 4, 1982

[54] BIOLOGICALLY PURE CULTURE OF ACTINOPLANES CAPABLE OF PRODUCING ANTIBIOTIC A/16686

[75] Inventors: Bruno Cavalleri; Hermes Pagani; Giancarlo Volpe, all of Milan, Italy

[73] Assignee: Gruppo Lepetit S.p.A., Milan, Italy

[21] Appl. No.: 215,310

[22] Filed: Dec. 11, 1980

Related U.S. Application Data

[62] Division of Ser. No. 135,560, Mar. 31, 1980, Pat. No. 4,303,646.

[30] Foreign Application Priority Data

Apr. 7, 1979 [GB] United Kingdom ............ 122298/79

[51] Int. Cl.³ .................. C12N 1/20; C12P 21/00; C12R 1/045
[52] U.S. Cl. .................................... 435/253; 435/68; 435/827
[58] Field of Search .................... 435/68, 253, 827

[56] References Cited

U.S. PATENT DOCUMENTS

4,001,397  1/1977  Celmer et al. .................. 435/68 X
4,038,383  7/1977  Celmer et al. .................. 435/68 X
4,169,887 10/1979  Celmer et al. .................. 435/827 X

FOREIGN PATENT DOCUMENTS

54-135703 10/1979  Japan ............................ 435/827

*Primary Examiner*—Lionel M. Shapiro

[57] ABSTRACT

The present invention relates to a glycopeptide antibiotic arbitrarily designated as A/16686 antibiotic, and to its physiologically-acceptable acid addition salts. Antibiotic A/16686 free base, and its acid addition salts are antibacterial agents, especially active against gramposititve microorganisms. The process for producing antibiotic A/16686 by culturing a novel strain of the actinoplanes genus, designated as Actinoplanes sp. ATCC 33076, is a further object of the present invention.

2 Claims, No Drawings

BIOLOGICALLY PURE CULTURE OF ACTINOPLANES CAPABLE OF PRODUCING ANTIBIOTIC A/16686

This is a division of application Ser. No. 135,560, filed Mar. 31, 1980 now U.S. Pat. No. 4,303,646 Dec. 1, 1981.

This invention relates to an antibiotic substance arbitrarily designated herein as A/16686 antibiotic, to a process for producing it by culturing a hitherto underscribed strain which has been characterized taxonomically as a novel strain of the Actinoplanes genus, and to its use as an antibacterial agent.

Antibiotic A/16686 is a glycopeptide antibiotic with a basic character which is capable of forming acid addition salts. Therefore the physiologically-acceptable acid addition salts of antibiotic A/16686 are part of this invention.

For simplicity in discussions of utility, the term "antibiotic A/16686" is used herein to refer to an antibiotic selected from antibiotic A/16686 free base and its physiologically-acceptable acid addition salts.

Antibiotic A/16686 inhibits in vitro the growth of certain pathogenic bacteria, especially gram-positive. Moreover parenteral administration of antibiotic A/16686 gives a high degree of protection against experimental infections in mice.

As stated above, antibiotic A/16686 is produced by culturing a novel strain of the Actinoplanes genus. A culture of this strain, which was isolated from a soil sample collected at Vaghalbod (India), has been deposited on Jan. 30, 1979 with the permanent culture collection of ATCC (American Type Culture Collection)-12301 Parklawn Drive, Rockville-Md. 20852-U.S.A. where it has been accorded the accession number ATCC 33076.

The characteristics of Actinoplanes sp. ATCC 33076 are given in the following paragraphs.

Morphology

The strain grows well on different media with a orange color of the substrate mycelium. It does not produce pigment. Aerial mycelium is always absent. At microscopic examination the vegetative mycelium reveals branched hyphae with a diameter of about 1 μm. The sporangia form scantly only on potato-agar and are globose with a very irregular surface and a diameter ranging from 5.0 to 9.0 μm. Sporangial release is observed after rupture of the wall of the sporangium. The subspherical spores are motile (1.0–1.5 μm diameter). Analysis of the cell-wall components reveals meso-diaminopimelic acid and sugar pattern of type D (Lechevalier et al.,—Chemical composition as a criterium in the classification of Actinomycetes. Adv. Applied Microbiology, 14, 1971. Academic Press N.Y.)

Cultural characteristics

Table 1 reports the cultural characteristics of Actinoplanes ATCC 33076 cultivated on various standard media suggested by Shirling and Gottlieb (Intern. J. System. Bact. 16, 313–340, 1966) and other media recommended by Waksman (The Actinomycetes, Vol. II-The Williams and Wilkins Co. 1961). The cultural characteristics were determined after 6 to 14 days of incubation at 30° C.

TABLE I

Cultural characteristics
The number of some of the culture media refers to those given by Shirling and Gottlieb in Methods for characterization of *Streptomyces* species - Intern. J. System. Bact. 16, 313–340, 1966.

| Culture media | Cultural characteristics |
|---|---|
| Medium No. 2 (yeast extract-malt agar) | Abundant growth, wrinkled surface, light brown 12 H 12 |
| Medium No. 3 (oatmeal agar) | Scant growth, thin, light orange 9 B 6 |
| Medium No. 4 (inorganic salts-starch agar) | Moderate growth, crusty surface, orange 11 L 12 |
| Medium No. 5 (glycerol-asparagine agar) | Scant growth, hyaline |
| Medium No. 6 (peptone-yeast extract-iron agar) | Scant growth, hyaline to light brown |
| Medium No. 7 (tyrosine agar) | Scant growth, smooth surface, brown 5 D 11 |
| Oatmeal agar (according to Waksman) | Abundant growth, wrinkled surface, orange to brown 12 C 10 |
| Hickey and Tresner's agar | Abundant growth, crusty surface, orange 11 G 8 |
| Czapek glucose agar | Moderate growth, crusty surface, orange 11 G 8 |
| Glucose asparagine agar | Scant growth, crusty surface light orange 11 F 6 |
| Nutrient agar | Moderate growth, smooth surface, orange 11 G 8 |
| Potato agar | Abundant growth, wrinkled surface, amber-brown 12 E 10 |
| Bennett's agar | Abundant growth, wrinkled surface, orange 11 C 8 |
| Calcium malate agar | Moderate growth, smooth surface, light orange 10 C 6 |
| Skim milk agar | Abundant growth, wrinkled surface, orange 9 C 2 |
| Czapek agar | Moderate growth, crusty surface, orange 10 D 7 |
| Egg agar | Moderate growth, smooth surface, hyaline to light orange |
| Peptone glucose agar | Abundant growth, wrinkled surface, orange 11 G 11 |
| Agar | Very scant growth, smooth surface, hyaline |
| Loeffler serum | Very scant growth, smooth surface, orange |
| Potato | Scant growth, crusty, light brown |
| Gelatin | Scant growth, light orange |
| Cellulose | Very scant growth, thin, hyaline |

Carbon utilization

Table II reports the utilization of carbon sources examined according to the method of Pridham and Gottlieb (J. Bact. 56, 107, 1948).

TABLE II

| Carbon sources | Utilization |
|---|---|
| Inositol | − |
| Fructose | + |
| Rhamnose | + |
| Mannitol | − |
| Xylose | + |
| Raffinose | − |
| Arabinose | + |
| Cellulose | − |
| Sucrose | + |
| Glucose | + |
| Mannose | + |
| Lactose | − |
| Salicin | + |

+ = positive utilization
− = no growth

Physiological characteristics

Table III reports the physiological characteristics of the strain.

TABLE III

| Test | Results |
| --- | --- |
| Hydrolysis of starch | positive |
| H$_2$S formation | positive |
| Tyrosinase reaction | negative |
| Casein hydrolysis | positive |
| Solubilization of calcium malate | negative |
| Liquefaction of gelatine | positive |
| Litmus milk — coagulation | positive |
| Litmus milk — peptonization | negative |
| Cellulose decomposition | negative |

For producing antibiotic A/16686 the strain Actinoplanes sp. ATCC 33076 is cultivated under aerobic conditions in an aqueous nutrient medium containing an assimilable source of carbon, an assimilable source of nitrogen and inorganic salts. Said culture medium can be anyone of a number of nutrient media usually employed in the fermentation art, however certain media are preferred. Thus, for instance, preferred carbon sources are glucose, fructose, mannose, sucrose and the like. Preferred nitrogen sources are soybean meal, peptone, meat extract, yeast extract, tryptone, amino acids and the like. Among the inorganic salts which can be incorporated in the culture media are the customary soluble salts capable of yielding sodium, potassium, iron, zinc, cobalt, magnesium, calcium, ammonium, chloride, carbonate, sulfate, nitrate and like ions. Ordinarily the antibiotic-producing strain is precultured in a shake flask, then the culture is used to inoculate jar fermentors for production of substantial quantities of antibiotic A/16686. The medium used for the preculture can be the same as that employed for larger fermentations, but other media can also be employed.

The A/16686-producing strain can be grown at temperatures between about 20' C. and about 37° C. and preferably at temperatures of about 28°–30° C.

During the fermentation, antibiotic production can be followed by testing samples of the broth or of extracts of the mycelial solids for antibiotic activity. Organisms known to be sensitive to antibiotic A/16686 are useful for this purposes. One especially useful assay organism is Sarcina lutea. The bioassay is conveniently performed by the agar diffusion method on agar plates. Maximum production of antibiotic activity generally occurs between about the third and the fifth days. The antibiotic produced during fermentation of the strain Actinoplanes sp. ATCC 33076 is found both in the broth and in the mycelial mass. Recovery of antibiotic A/16686 may therefore, be carried out by separated extraction of broth and mycelium.

Extraction of the mycelial mass is best accomplished with methanol, but other lower alcohols and chloroform are also suitable. Antibiotic A/16686 is recovered as a raw product from the extracting solvent by routine procedure. Analogously, also the broth is extracted-preferably with n-butanol—and a further amount of raw antibiotic A/16686 is obtained by precipitation from this solution. Purification of the raw antibiotic A/16686 is then achieved by treating the product recovered from the extracting solvents with a mixture chloroform:ethanol:water 4:7:2, separating the oily product which forms and pouring it in water. This treatment causes solidification of the product which is recovered by filtration, and further purified by Silicagel column chromatography eluting with a mixture acetonitrile: 0.01 N HCl 1:1. Antibiotic A/16686, which according to this procedure is recovered in the form of the hydrochloride, is then desalted by chromatography on a crosslinked dextran gel column.

Each step of the above purification procedure is monitored by thin-layer chromatography using a suitable solvent system such as a basic solvent system, for instance n-propanol:n-butanol:N-ammonium hydroxide 2:3:4 (upper phase) or methanol: 10% aqueous ammonium acetate: 10% ammonium hydroxide 10:9:1, in which any acid addition salt of antibiotic A/16686 is converted into the free base. All the above steps are therefore aimed to isolate pure antibiotic A/16686 characterized by a particular $R_f$ value in the particular solvent system employed.

Other purification methods may suitably be employed involving conventional extraction and adsorption procedures. Said alternative methods may be easily set up, step by step, by monitoring the purification progress by thin-layer chromatography, as described above. Following the t.l.c. spot of antibiotic A/16686 with a particular $R_f$ value, it will thus be apparent to any skilled technician which operations might suitably be carried out in order to isolate pure antibiotic A/16686.

If desired the pure antibiotic A/16686 hydrochloride, obtained according to the procedure set forth above, may then be converted into the corresponding free base or into another physiologically-acceptable acid addition salt by common procedures.

Antibiotic A/16686 is an antimicrobial agent and it is especially active against gram-positive microorganisms. In particular, the in vitro activity spectrum of antibiotic A/16686 is summarized in the following Table IV:

TABLE IV

| Organisms | M.I.C. (µg/ml) Antibiotic A/16686 |
| --- | --- |
| S. aureus ATCC 6538 | 0.16 |
| S. aureus ATCC 9144 | 0.16 |
| S. aureus Tour | 0.31 |
| Staphylococcus 10B Ciba | 0.08 |
| S. epidermidis ATCC 12228 | 0.08 |
| S. saprophyticus NCTC 7292 | 0.16 |
| M. flavus ATCC 10240 | 0.016 |
| S. lutea ATCC 9341 | 0.02 |
| S. pyogenes C 203 SKF 13400 | 0.01 |
| S. pneumoniae Felton UC 41 | 0.05 |
| S. faecalis ATCC 7080 | 0.31 |
| S. foecium ATCC 10541 | 0.08 |
| S. agalactiae ATCC 7077 | 0.02 |
| S. mutans ATCC 27607 | 0.08 |
| C. diphtheriae var.mitis ATCC 11051 | 0.31 |
| C. xerosis NCTC 9755 | 0.02 |
| B. subtilis ATCC 6633 | 0.062 |
| B. cereus var.mycoides ATCC 11778 | 0.08 |
| C. perfringens ISS 30543 | 0.16 |
| P. acnes ATCC 6919 | 0.4 |
| P. acnes ATCC 6922 | 0.8 |
| P. acnes ATCC 25746 | 0.4 |

Table V reports the results of tests wherein antibiotic A/16686 tested against a variety of Staphylococcus aureus, Streptococcus pyogenes, Streptococcus pneumoniae and Streptococcus faecalis strains clinically isolated.

TABLE V

| Organisms | M.I.C. (μg/ml) Antibiotic A/16686 |
|---|---|
| S. aureus 54310 L 1096 | 0.62 |
| S. aureus 54560/I L 1097 | 0.31 |
| S. aureus 54635 L 1098 | 0.31 |
| S. pyogenes L 33 | 0.04 |
| S. pyogenes L 794 | 0.08 |
| S. pyogenes L 800 | 0.04 |
| S. pyogenes L 801 | 0.16 |
| S. pyogenes L 802 | 0.08 |
| S. pyogenes L 803 | 0.08 |
| S. pyogenes L 804 | 0.62 |
| S. pyogenes L 805 | 0.08 |
| S. pneumoniae L 1055 | 0.04 |
| S. pneumoniae L 1102 | 0.04 |
| S. pneumoniae L 1174 | 0.08 |
| S. faecalis L 768 | 0.31 |
| S. faecalis L 876 | 0.31 |
| S. faecalis L 922 | 0.31 |
| S. faecalis L 949 | 0.31 |
| S. faecalis L 965 | 0.31 |
| S. faecalis L 1139 | 0.62 |
| S. foecium L 763 | 0.16 |

Antibiotic A/16686 has also been found to possess a high order of activity in vivo against various pathogenic organisms. The effectiveness of antibiotic A/16686 is readily apparent from Table VI which gives the ED50 values in mice against three different microorganisms.

TABLE VI

| | ED$_{50}$ mg/kg s.c. | | |
|---|---|---|---|
| | S.aureus Tour | S.pyogenes C203 ISM | S.pneumoniae Felton UC 41 |
| A/16686 | 24.6 | 0.09 | 0.2 |

Antibiotic A/16686 has been found to possees a relatively low level of toxicity when used in test animals. For example, the LD$_{50}$ value, when the antibiotic is administered intraperitoneally to mice is approximately comprised between 500 and 750 mg/Kg.

A further object of the present invention is therefore the use of antibiotic A/16686 as an antibacterial agent, intending with the term "use" all industrially applicable aspects and acts of said use, including the embodying of antibiotic A/16686 into pharmaceutical compositions, which therefore represent a further feature of the present invention.

These pharmaceutical compositions, suitable for oral, topical or parenteral administrations, are prepared in the usual ways known to all skilled in the pharmaceutical sciences. Examples of these formulations are described for instance in Remington's Pharmaceutical Sciences 15$^{th}$ Ed., 1975 Mack Publishing Co. Easton, Pa. These forms include tablets, capsules, powders, ointments, liquid solutions, solutions for injection and the like. The dosage unit may contain from 0.5 to 99 percent, preferably from 5 to 80 percent of active ingredient. The daily dosage may be set up considering several factors such as the body weight, the infecting organism, the severity of the infection, the period and the mode of administration.

In order to illustrate more fully the operation of this invention, the following examples are provided.

EXAMPLE 1

Fermentation of the strain Actinoplanes sp. ATCC 33076

A culture of Actinoplanes sp. ATCC 33076 is precultured by growing the strain in a shake-flask culture having the following composition

| meat extract | 3 g/l |
|---|---|
| yeast extract | 5 g/l |
| tryptone | 5 g/l |
| soluble starch | 24 g/l |
| glucose | 1 g/l |
| CaCO$_3$ | 4 g/l |
| Tap water | 1 liter |

The flasks are shaken for about 96 hours at 28°–30° C. and then the pre-cultures (1 liter) are used to inoculate the jar fermentors each containing 10 liters of the following nutrient medium

| Meat extract | 40 g |
|---|---|
| Peptone | 40 g |
| Yeast extract | 10 g |
| Sodium chloride | 25 g |
| Soybean meal | 100 g |
| Glucose | 250 g |
| CaCO$_3$ | 50 g |
| Tap water | 10 liters |

The fermentation batches are incubated aerobically under stirring at 28°–30° C. At intervals, the antibiotic activity is assayed microbiologically by the agar diffusion method using Sarcina lutea as the test organiism. The maximum activity is reached after 72 to 120 hours of fermentation.

EXAMPLE 2

Recovery of antibiotic A/16686

Whole fermentation broth (170 l) prepared as described in Example 1 is cooled at 10° C. and brought to pH 3.5 by means of 18% HCl. The resulting acidic broth is filtered using a filter aid (Clarcel Flow-Ma), and the mycelial cake is washed with water. Then the filtered broth and the mycelium are further processed separately.

(a) Methanol (30 l) is used to extract the mycelial mass which, after filtration, is extracted again with a mixture methanol/water (30 l of methanol plus 5 l of water). The exhausted mycelium is discarded and the two methanol extracts are concentrated under vacuum at a temperature lower than 40° C. to yield an aqueous concentrate (6 l). This aqueous concentrate is extracted with three portions, 10 l each, of n-butanol, which are combined and concentrated to a small volume under vacuum.

This concentrate is added to petroleum ether and the resulting precipitate is separated by decantation and added to a further amount of petroleum ether. The precipitate is separated by filtration and dried under vacuum at room temperature to give 80 g of antibiotic A/16686 as a raw material having a M.I.C. against S. pneumoniae UC 41 of 0.1 μg/ml.

(b) The filtered broth plus washing (165 l) is cooled to 10° C. and adjusted to pH 3.5 by addition of concentrated HCl (2.5 l). The obtained solution is extracted with n-butanol (80 l) and the organic extract is then concentrated under vacuum at a temperature lower than 35° C., to give a butanol concentrate (6 l). This concentrate is added to petroleum ether and the obtained precipitate, separated by decantation is added to a further amount of petroleum ether. The solid is separated by filtration and dried under vacuum at room temperature to give 26.3 g of raw antibiotic A/16686 having a M.I.C. against *S. pneumoniae* UC 41 of 0.8 μg/ml.

EXAMPLE 3

Purification of antibiotic A/16686

47.7 g of the raw antibiotic A/16686 obtained in Example 2a) are treated with 1.4 l of a chloroform:ethanol:water mixture (4:7:2) (v/v/v) and the oily product which forms is separated from the solution by decantion. Further 70 ml of the above mixture are then added to the oily product and the separation is repeated. By treatment of the oily product with water (440 ml), it solidifies and is separated by centrifugation and filtration:

(a) The solid, which is separated, is suspended in water (170 ml), dissolved by addition of methanol (400 ml) and filtered. Then the solvents are stripped under vacuum by adding n-butanol at a temperature never higher than 35° C., to give a butanol concentrate of about 50 ml. By addition of diethyl ether (500 ml) a precipitate forms which is separated by filtration and dried under vacuum at room temperature yielding 1.012 g of rather pure antibiotic A/16686 having a M.I.C. on *S. pyogenes* of 0.025 μg/ml. The rather pure antibiotic A/16686 so obtained is then submitted to the following purification procedures:

1.58 g of the above antibiotic A.16686 characterized by a M.I.C. against *S. pyogenes* of 0.025 μg/ml are dissolved in acetonitrile:water 1:1 (v/v) and the resulting solution is applied to a column containing 430 g of silica gel 60 (Merck 0.06–0.2 mm) prepared in the same mixture. The column is developed first using the same acetonitrile-water mixture and collecting 70 fractions of 20 ml each, and then using acetonitrile: N/100 HCl 1:1 (v/v) and collecting further 290 fractions, of 20 ml each. Elution of the column is monitored by thin layer chromatography on 60 $F_{254}$ silica gel plates and by assaying fractions against *Sarcina lutea*. Fractions 130 to 265 are combined and the solvents are stripped under vacuum with n-butanol to give a n-butanol concentrate of 20 ml. This residual volume is poured into a large amount of ethyl ether and the precipitate which forms is separated by filtration and dried under vacuum at room temperature over $P_2O_5$ yielding 1.015 g of antibiotic A/16686.

0.67 g of the above substance are dissolved in 24 ml of water and 76 ml of methanol. The resulting solution is applied to a 3.0×62.0 cm column containing 220 g of Sephadex LH-20, prepared in methanol:water 7:3 (v/v). The column is developed with the same mixture collecting 10 ml fractions. Fractions 24 to 32 are combined and the solvents are stripped under vacuum at a temperature lower than 35° C. with n-butanol to a residual butanol volume of about 10 ml. This solution is added to ethyl ether to precipitate the desired pure antibiotic A/16686. The precipitate is separated by filtration washed with ethyl ether and dried under vacuum over $P_2O_5$ at room temperature yielding 0.26 g of pure antibiotic A/16686.

(b) The filtrate is stripped under vacuum at a temperature lower than 35° C. by adding n-butanol, to give a n-butanol concentrate of 50 ml. By addition of petroleum ether a precipitate forms which is separated by filtration and dried under vacuum at room temperature yielding 42.9 g of partially purified antibiotic A/16686 characterized by a M.I.C. value against *S. pyogenes* of 0.2 μg/ml. This antibiotic substance is suspended in water (2.5 l) and dissolved by addition of NaOH 1 N up to pH 7. Then the obtained aqueous solution is extracted with three portions, 5 l each, of n-butanol and this organic phase, after being washed with water, is concentrated to 200 ml under vacuum at a temperature lower than 35° C.

By adding diethyl ether to the concentrate, a precipitate forms which is filtered and dried under vacuum at room temperature. The dried product is dissolved in 160 ml of the upper layer of a n-propanol:n-butanol-1 N ammonium hydroxyde mixture 2:3:4 (v/v/v). The resulting solution is applied to a 100 cm high column, 7.5 cm in diameter, containing 1.7 Kg of silica gel 60 (Merck 0.06–0.2 mm) prepared in the above solvents mixture. The column is developed using the same mixture collecting 300 ml fractions. Elution of the column is monitored by thin layer chromatography. Fractions 21 to 26 are combined and stripped under vacuum at a temperature lower than 35° C. with n-butanol to give a n-butanol concentrate of 50 ml. By addition of diethyl ether a precipitate forms which is separated by filtration, washed with diethyl ether and dried under vacuum over $P_2O_5$ at room temperature. A 1.875 g crop of rather pure antibiotic A/16686 is obtained which is then further purified by following the same procedures described under a) above.

Antibiotic A/16686 as the hydrochloride, is a white, crystalline material slightly hydroscopic which melts at 224°–226° C. It is very soluble in water and dimethylformamide, soluble in methanol, ethanol, propanol and butanol, but is insoluble in ethyl ether, petroleum ether and benzene. Elemental analysis of antibiotic A/16686 hydrochloride, previously dried at 140° C. under inert atmosphere, indicates the following approximate percentage composition (as an average of several analyses): carbon 51.73%; hydrogen 6.34%; nitrogen 9.96%; chlorine (total content) 5.84%; chlorine ions 4.74%; and residue 1%. The infrared absorption spectrum was determined in nujol.

The following absorption maxima are observed (in $cm^{-1}$): 3290–3070, 2930 and 2860 (nujol), 1765, 1630, 1510, 1455, 1375 (nujol), 1230, 1175, 1130, 1065, 1030, 1015, 980, 840 and 820.

The ultraviolet absorption spectrum exhibits the following absorption maxima:

| | | |
|---|---|---|
| (a) in methanol | | |
| | 232 nm | ($E_{1cm}^{1\%}$ = 178) |
| | 265 nm | ($E_{1cm}^{1\%}$ = 107) |
| (b) in methanol containing 0.1N HCl | | |
| | 231 nm | ($E_{1cm}^{1\%}$ = 167) |
| | 270 nm | ($E_{1cm}^{1\%}$ = 96) |
| (c) in methanol containing 0.1N NaOH | | |
| | 250 nm | ($E_{1cm}^{1\%}$ = 232) |
| | 295 nm | (shoulder) |
| (d) in methanol containing pH 7.38 buffer | | |
| | 231 nm | ($E_{1cm}^{1\%}$ = 167) |
| | 270 nm | ($E_{1cm}^{1\%}$ = 96) |

The ultraviolet absorption spectra were registered with a Beckmann DK-2 Spectrophotometer). Antibiotic A/16686 hydrochloride has a specific rotation, $[\alpha]_D^{24}$, of +49.7° (c=0.43% in DMF).

Antibiotic A/16686 shows the following characteristic reaction:

| | |
|---|---|
| ninhydrin (3% ethanolic solution) | negative |
| ninhydrin (3% ethanolic solution + sodium acetate) | positive |
| 1% FeCl₃ — 1% K₃Fe(CN)₆ (aqueous solution) | positive (green) |
| Molisch | positive |
| Fehling | negative |
| Biuret | positive |
| Anthrone | positive |
| Millon | negative |
| H₂SO₄ conc | negative |
| KMnO₄ aqueous | positive |

The $R_f$ values of antibiotic A/16686 in paper chromatography using different elution systems and *S. aureus* ATCC 6538 as a detection organism, are given in the following Table:

TABLE VII

Chromatographic behaviour (Whatman Nr. 1 paper)* of antibiotic A/16686

| Elution systems | $R_f$ values |
|---|---|
| (1) n-butanol saturated with Sorensen buffer pH 6.0 | 0.00 |
| (2) n-butanol saturated with water containing 2% of p-toluenesulfonic acid | 0.00 |
| (3) n-butanol saturated with water containing 2% ammonium hydroxide | 0.00 |
| (4) Sorensen buffer, pH 6.0, saturated with n-butanol | 0.05 |
| (5) n-butanol:methanol:water 4:1:2 | 0.43 |
| (6) ethyl acetate saturated with water | 0.00 |
| (7) n-butanol:acetic acid:water 2:1:1 | 0.52 |
| (8) n-butanol:pyridine:water 4:3:7 | 0.87 |

*Descending chromatography

Rm: 40 cm

Amounts: 20 μg of the compound dissolved in water methanol (2 mg/ml)

The $R_f$ values of antibiotic A/16686 in various thin-layer chromatography systems are listed in the following table (the conditions are indicated below the table):

TABLE VIII

| | Elution systems (v/v/v) | $R_f$ values |
|---|---|---|
| (1) | n-propanol:n-butanol:N ammonium hydroxide 2:3:4 (upper phase) | 0.15 |
| (2) | n-butanol:acetic acid:water 4:2:5 | 0.61 |
| (3) | n-butanol:ethanol:0.1 N hydrochloric acid | 0.61 |
| (4) | chloroform:ethanol:10% acetic acid 4:7:2 | 0.00 |
| (5) | n-butanol:acetic acid:water 4:1:5 | 0.17 |
| (6) | methanol:10% aqueous ammonium acetate:10% ammonium hydroxide 10:9:1 | 0.52 |
| (7) | n-butanol:pyridine:water:acetic acid 6:4:3:1 | 0.45 |
| (8) | methanol:10% aqueous ammonium acetate:10% ammonium hydroxide 10:9:1 | 0.11 |
| (9) | 0.25 M aqueous NaH₂PO₄:acetonitrile 1:1 | |
| (10) | methanol:10% aqueous ammonium acetate 1:1 | 0.65 |
| (11) | n-butanol:acetic acid:water 4:2:5 | 0.77 |

Rm: about 140 mm

Amounts: 2÷5 μl of a solution (1 mg/ml) of the compound in acetonitrile-water 1:1

Visualization:
(a) bioautography on agar plates seeds with *B. subtilis* ATCC 6633; (b) carbonization by heating with α-naphthol-sulfuric acid; (c) Jodine vapour; (d) chlorine-toluidine reagent; (e) UV-light at 254 nm 1 to 7-Silicagel 60 F₂₅₄ plates (Merck); Visualization a, e, b, c, d, e 8,9-Silicagel 60 F₂₅₄ silanised (Merck); Visualization e 10, 11-Cellulose F plates (Merck); Visualization a, As determined through high performance chromatographic techniques, antibiotic A/16686, isolated and purified as described in Example 3, consists of a main component which amounts to 70–80%, while the remaining 30–20 % is ascribable to al least two minor components. Antibiotic A/16686 hydrochloride isolated as described in the preceeding examples is the hydrochloride of a chlorine-containing basic glycopeptide which differs from antibiotics belonging to the classical glycopeptide group in containing chlorine and in the variety of its amino-acids components. In fact amino-acid analysis of antibiotic A/16686, after acid hydrolysis is 6 N hydrochloric acid at 110° C. for 6 hours, by means of an amino-acid authoanalyzer, indicated the presence of the following amino-acids: ornithine (118 μg/mg=0.58 μM/mg), aspartic acid (29.2 μg/mg=0.22 μM/mg), threonine (68 μg/mg=0.57 μM/mg), glycine (25 μg/mg=0.33 μM/mg), alanine (29 μg/mg=0.32 μM/mg), leucine (41 μg/mg=0.31 μM/mg) and phenylalanine (42 μg/mg=0.25 μM/mg). Further four peaks were detected using the column for neutral and acidic amino acids. Two of these four amino-acids were identified by means of gas chromatography-mass spectrometry after conversion into their corresponding methyl ester-trifluoroacetyl derivatives and were assigned the following structures:

OH                OH       Cl

[phenyl ring]    [phenyl ring]

CH—NH₂           CH—NH₂
|                |
COOH  I          COOH  II

EXAMPLE 4

Isolation of the free base

By treatment of a solution of antibiotic A/16686 hydrochloride (0.05 g) in water (3 ml)—ethanol (8 ml) with 1,2-epoxybutane (2 ml) a precipitate forms which after standing at low temperature for one day is separated by centrifugation, washed with ethanol and dried over P₂O₅ under vacuum at room temperature yielding 0.016 of the corresponding free base.

Treatment of said free basic form of antibiotic A/16686 with a pharmaceutically acceptable inorganic or organic acid leads to the formation of a corresponding acid addition salt. Pharmaceutically acceptable acids are non-toxic acids that are suitable for the formation of therapeutically useful salts as known in the art such as for instance hydrochloric, hydrobromic, sulfuric, phosphoric, nitric, tartaric, acetic, succinic, lactic, glutamic or methanesulphonic acid.

We claim:

1. A biologically pure culture of Actinoplanes sp. ATCC 33076 and a nutrient medium consisting of an assimilable source of each of carbon, nitrogen, and essential mineral salts, said culture being capable of producing antibiotic A/16686 in a recoverable quantity upon fermentation.

2. A biologically pure culture of Actinoplanes sp. ATCC 33076, capable of producing antibiotic A/16686.

* * * * *

UNITED STATES PATENT AND TRADEMARK OFFICE
CERTIFICATE OF CORRECTION

PATENT NO. : 4,328,316

DATED : May 4, 1982

INVENTOR(S) : Bruno Cavalleri, et al.

It is certified that error appears in the above—identified patent and that said Letters Patent is hereby corrected as shown below:

Column 3, Table III, an arrow should be drawn in as shown below:

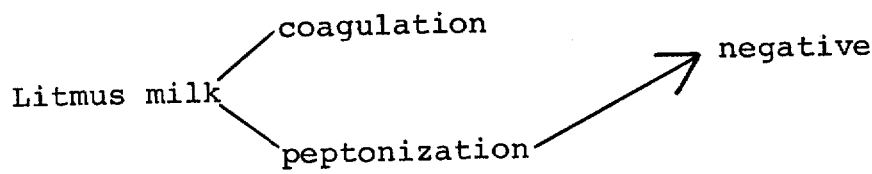

Column 3, line 41, "20'" should read --20°--.

Column 5, line 39, "possees" should read --possess--.

Column 6, line 34, "organiism" should read --organism--.

Column 9, Table VIII, line (9), under subheading "$R_f$ values" should read, --0.68--.

Column 10, line 18, "is" should read --in--.

Signed and Sealed this

Seventh Day of September 1982

[SEAL]

Attest:

GERALD J. MOSSINGHOFF

Attesting Officer

Commissioner of Patents and Trademarks